(12) United States Patent
Inwald et al.

(10) Patent No.: US 12,293,815 B2
(45) Date of Patent: *May 6, 2025

(54) SMART MULTIDOSING

(71) Applicant: OptimDosing LLC, Farmington Hills, MI (US)

(72) Inventors: David Inwald, Berkley, MI (US); Kenneth I. Kohn, West Bloomfield, MI (US); Laura S. Dellal, New York, NY (US); Caitlin Joline Brown, Ashburn, VA (US)

(73) Assignee: OptimDosing LLC, Farmington Hills, MI (US)

( * ) Notice: Subject to any disclaimer, the term of this patent is extended or adjusted under 35 U.S.C. 154(b) by 154 days.

This patent is subject to a terminal disclaimer.

(21) Appl. No.: 17/230,424

(22) Filed: Apr. 14, 2021

(65) Prior Publication Data

US 2021/0319870 A1    Oct. 14, 2021

Related U.S. Application Data

(60) Provisional application No. 63/009,483, filed on Apr. 14, 2020.

(51) Int. Cl.
| | |
|---|---|
| *G06Q 50/00* | (2024.01) |
| *A61J 7/00* | (2006.01) |
| *A61K 31/7088* | (2006.01) |
| *A61K 38/46* | (2006.01) |
| *A61K 48/00* | (2006.01) |
| *G16H 20/10* | (2018.01) |

(Continued)

(52) U.S. Cl.
CPC ............ *G16H 20/10* (2018.01); *A61J 7/0084* (2013.01); *A61K 31/7088* (2013.01); *A61K 38/465* (2013.01); *A61K 48/0091* (2013.01); *G16H 50/20* (2018.01); *G16H 50/70* (2018.01); *G16H 70/40* (2018.01)

(58) Field of Classification Search
CPC ........ G16H 20/10; G16H 20/00; G16H 70/00; G16H 50/70; G16H 70/40; G16H 40/60; G16H 50/20

See application file for complete search history.

(56) References Cited

U.S. PATENT DOCUMENTS

| | | | | |
|---|---|---|---|---|
| 11,367,519 | B1 * | 6/2022 | Heldman | ............... A61M 5/142 |
| 12,009,109 | B2 * | 6/2024 | Inwald | ................... G16H 10/60 |

(Continued)

*Primary Examiner* — Rajesh Khattar (74) *Attorney, Agent, or Firm* — Kohn & Associates PLLC; Kenneth I. Kohn; Laura S. Dellal (57) ABSTRACT

A method of dosing multiple drugs for an individual patient, by collecting data from the individual patient including drugs to be taken by the patient and genetic testing information, analyzing the individual patient data in view of dosing criteria established based on outside patient data, and determining doses of multiple drugs for each drug taken by the individual patient. A logic engine for dosing multiple drugs, including an algorithm stored on non-transitory computer readable media for collecting outside data to establish criteria for dosing multiple drugs to an individual patient and storing the outside data and individual patient data in a database, analyzing the individual patient data in view of criteria established from the outside data, and determining a dose for each drug to be taken.

15 Claims, 4 Drawing Sheets

(51) Int. Cl.
*G16H 50/20* (2018.01)
*G16H 50/70* (2018.01)
*G16H 70/40* (2018.01)

(56) References Cited

U.S. PATENT DOCUMENTS

| | | | |
|---|---|---|---|
| 2008/0008991 A1* | 1/2008 | Groen | G16H 20/10 |
| | | | 435/5 |
| 2015/0265628 A1* | 9/2015 | Rosenblatt | A61K 31/5513 |
| | | | 702/19 |
| 2018/0001184 A1* | 1/2018 | Tran | G16H 50/20 |
| 2020/0181619 A1* | 6/2020 | Tang | C12N 9/22 |
| 2020/0245925 A1* | 8/2020 | Inwald | G16H 30/20 |

* cited by examiner

SMART MULTIDOSING

BACKGROUND OF THE INVENTION

1. Technical Field

The present invention relates to methods of determining dosing of drugs. More specifically, the present invention relates to methods, software, and algorithms for determining single and multiple drug doses for an individual patient or a patient population based on compilation and analysis of clinical study data.

2. Background Art

Many individuals, especially as they age, need to take multiple drugs for different indications. Taking multiple drugs comes with risks, because drug interactions can cause unwanted and harmful side effects, and even cognitive side effects that can impact daily activities. In the time period of 2011-2014, the CDC states that 23.1% of individuals used three or more prescription drugs in the past 30 days, and 11.9% used five or more prescription drugs in the past 30 days. Over 40% of individuals over 65 years old are taking five or more drugs daily. Many individuals who also decide on an appropriate dose for themselves (such as increasing a dose) without doctor input can also inadvertently cause a reaction with other drugs that they self-administer. Even doctors may not be aware of drug interactions, and it is usually up to the individual to ask a pharmacist of any potential problems. Many individuals also take over-the-counter drugs, vitamins, and supplements without thinking that they may have an impact on each other and/or on prescription drugs.

Quinn, et al. (Sci. Data. 2017; 4: 170167) states that half of patients taking prescription drugs are taking two or more, and 5% take eight or more, and most multidrug combinations are used for treating metabolic syndrome. Quinn, et al. studied insurance claims to determine the number of prescription drugs patients are taking within a 30-day window that overlap. Table 3 in Quinn, et al. details the 3-drug combinations that are most represented prior to emergency department visits. Table 4 details the most common and overrepresented drug ingredient co-exposures with metformin or oxycodone.

Online drug interaction checkers exist, such as Drugs-.com, and websites like these can provide warnings of interactions with a drug that an individual is taking. A list of side effects is generated for each combination of drugs. However, there is no information as to whether a particular dose causes an effect, or what dose the individual should take based on the combination of drugs that the individual is already taking.

U.S. Pat. No. 6,658,396 to Tang, et al. discloses neural networks that are trained on historical data, and used to predict any of (1) optimal patient dosage of a single drug, (2) optimal patient dosage of one drug in respect of the patient's concurrent usage of another drug, (3a) optimal patient drug dosage in respect of diverse patient characteristics, (3b) sensitivity of recommended patient drug dosage to the patient characteristics, (4a) expected outcome versus patient drug dosage, (4b) sensitivity of the expected outcome to variant drug dosage(s), (5) expected outcome(s) from drug dosage(s) other than the projected optimal dosage. Both human and economic costs of both optimal and sub-optimal drug therapies may be extrapolated from the exercise of various optimized and trained neural networks. Heretofore little recognized sensitivities—such as, for example, patient race in the administration of psychotropic drugs—are made manifest. Individual prescribing physicians employing deviant patterns of drug therapy may be recognized. Although not intended to prescribe drugs, nor even to set prescription drug dosage, the neural networks are very sophisticated and authoritative "helps" to physicians, and to physician reviewers, in answering "what if" questions. However, Tang, et al. cannot analyze multiple drugs in combination.

Therefore, there remains a need for an effective method of managing multiple drugs and suggesting appropriate doses based on the combination of drugs being taken.

SUMMARY OF THE INVENTION

The present invention provides for a method of dosing multiple drugs for an individual patient, by collecting data from the individual patient including drugs to be taken by the patient and genetic testing information, analyzing the individual patient data in view of dosing criteria established based on outside patient data, and determining doses of multiple drugs for each drug taken by the individual patient.

The present invention further provides for a logic engine for dosing multiple drugs, including an algorithm stored on non-transitory computer readable media for collecting outside data to establish criteria for dosing multiple drugs to an individual patient and storing the outside data and individual patient data in a database, analyzing the individual patient data in view of criteria established from the outside data, and determining a dose for each drug to be taken.

DESCRIPTION OF THE DRAWINGS

Other advantages of the present invention are readily appreciated as the same becomes better understood by reference to the following detailed description when considered in connection with the accompanying drawings wherein.

DETAILED DESCRIPTION OF THE INVENTION

Figure 1:
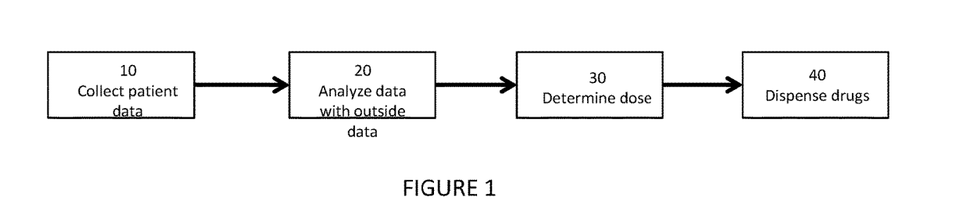
FIG. 1 is a schematic of the method of the present invention.

The present invention generally provides for methods of dosing multiple drugs when taken together to ensure that patients receive a safe and effective dose of each drug. Most generally, as shown in FIG. 1, the method includes collecting patient data 10 with treatment plan details including drugs to be taken, analyzing the data in view of outside data 20, and determining a dose for each drug with output data 30. The dose determination is an optimization of maximizing therapeutic effect while minimizing likelihood of adverse effects for the combination of drugs taken. This will consider data relating to pharmacokinetics, distribution, prior toxicity and efficacy determinations, age, metabolism, and any other criteria related to toxicity and efficacy outcomes. In other words, known data is compiled from prior clinical data studies (Phase 1 through Phase 4 trials) and compared to specific patient data in order to predict proper safe and efficacious dosing of multiple drugs. The method can further include dispensing the drugs to the patient in the prescribed dose 40. In the case of dispensing, the present invention ensures sufficient evaluation criteria was provided before suggesting an outcome. The present invention further provides for a logic engine (i.e., a computer program) for performing the method, including an algorithm stored on non-transitory computer readable media for collecting patient data 10 and storing the patient data in a database 50, analyzing the patient data in view of outside data 20, and determining a dose for each drug with output data 30.

Most generally, the algorithm used in the present invention is Data Input→Central AI3<-> Healthcare Professional. The data input can be from, but is not limited to, clinics, electronic medical records (EMRs), pharmaceutical companies, private databases, or CROs. The healthcare professional can be, but is not limited to, an MD, pharmacist, hospital, insurer, nurse, laboratory professional, or other medical professional. The healthcare professional can then input data regarding the patient back into the central AI such as, but not limited to, patient data from monitors (including at a medical facility and personal monitors such as smart devices), data from EMRs, insurance information. Any of the data being collected and received can be in real time. From the data input to the central AI, the AI creates a multidimensional matrix relating any and all variables that effect drug metabolism, with dimensions relating how these variables are affected by dosing of additional consumed drugs.

The AI applies a predeveloped matrix to a patient's specific physiology, metabolism, etc. for drugs being taken. As these factors can be induced to change by a change in disease state, drug induced changes, etc., real time monitoring of these changes can assist in real time drug dosing adjustments. While such a system may not be practical for all home care but is practical for patients already on monitors and mechanically/digitally receiving drugs.

The system is drug centric. The AI creates a matrix relating dosing to patient condition and effect of other drugs on that condition which effect efficacy of all drugs taken, and toxicity of all drugs taken. The AI can generate matrices of matrices to handle complicated multivariable relationships with simple output of recommended dosing range of the multiple drugs, or actually in real time administer those drugs. The general factors/variables in the matrix can be, but are not limited to, age of patient, weight of patient, known side effects of drugs alone and in combinations with other drugs, known toxicity range as related to ED 50 and other dose response points of interest, efficacy ranges, and chronic treatment effect versus acute treatment (one-time dosing versus dosing over time). Such factors can be gathered from clinical studies along with other information as necessary and then the patient can be fit into matrix to determine dosing for drugs needed.

Figure 2:
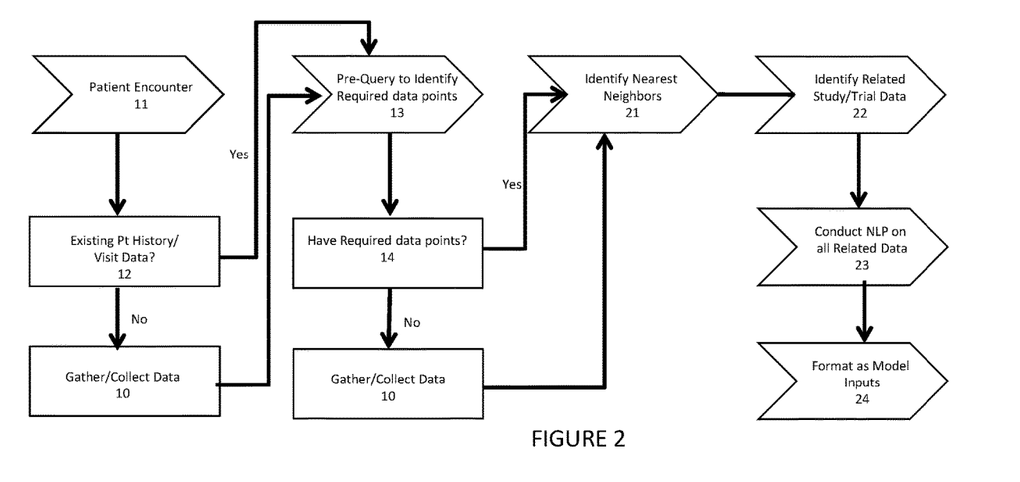
FIG. 2 is a schematic of the method of the present invention.
Figure 4:
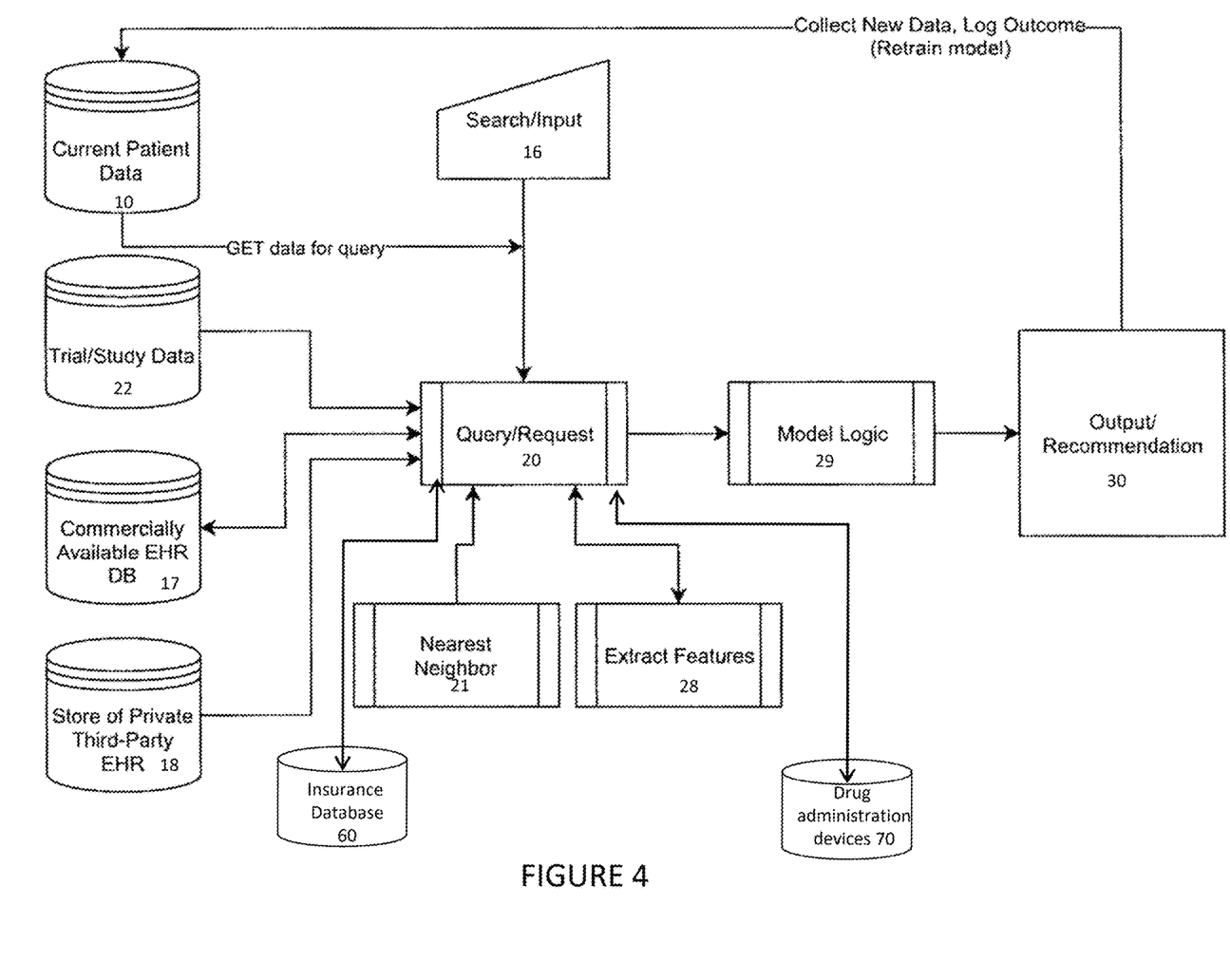
FIG. 4 is a schematic of the method of the present invention.

The method and logic engine are shown in greater detail in FIGS. 2 and 4. At a patient encounter 11, it is first determined if there is any existing fit history or visit data 12. If not, patient data can be collected 10 as detailed below. A pre-query 13 is performed to identify any required data points to perform an analysis. If the required data points 14 are not present, then they are gathered or collected 15. Next, the nearest neighbors are identified 21, related study/trial data is identified 22, Natural Language Processing (NLP) is conducted on related unstructured data 23, before being conditioned as program inputs 24. Natural Language Processing is a type of AI that extracts features from unstructured text, such as, but not limited to, patient notes or items appearing in 'other' categories in drug trials. The unstructured data can also list additional side effects or notes from any informal exams.

Various data is collected about the patient 10 and entered into a database 50 on computer readable media. This includes symptoms, diagnoses, and proposed drugs/treatments 16 that the patient has been prescribed to take by a doctor or other medical professional. More specific data can be collected from analysis of blood and urine samples related infectious disease, metabolism, presence of antigen indicated disease (such as cancer, MS, etc.), patient temperature, blood pressure and other data routinely or additionally collected by the health care professional or present in the patient's electronic health record.

Fixed demographics can be collected, such as, but not limited to, age, gender, race, height, known drug interactions, and body composition (fat, muscle content). All of these criteria, including genetic inclination to drug metabolism and general metabolism, resistance and susceptibility to disease, and other related criteria are analyzed, as each can be individually pertinent related to the metabolism of each individual drug prescribed and taken by the patient, as well as the combined effects of each of the drugs on each other. In other words, consideration is considered regarding the drugs individual effects on the patient as well as the effects of the combined combination of drugs being taken.

Temporal values can be collected, such as, but not limited to, historic values from existing electronic medical records (EMR) or electronic health records (EHR), current/up to date values, cholesterol, blood pressure, weight, and diagnostics related to a specific ongoing disease. The database 50 can be in electrical connection with commercially available EHR databases 17 and private third-party EHR databases 18 to search for relevant data and extract data to the database 50 for analysis. Patient data related to diet (i.e., specific foods eaten often, especially ones known to have interactions with drugs) and nutritional supplements can also be collected, as well as exercise habits.

Genetic components can be collected, such as, but not limited to, key genetic markers, whole genome data from genetic testing/ancestry sites, or test results from any type of genetic tests. Genetic components are important not just for markers for known drug efficacy, but also for generating ethnicity and demographics features for multidimensional nearest neighbor calculations (further described below). The known effects of drugs on liver enzymes, critical to first pass drug metabolism will be considered and analyzed as each drug alone and in combination effects the liver enzymes differently, so the capacity of the patient's liver enzymes as well as the drug effect on the liver enzymes are synthesized in the analysis. Genetic testing results can be obtained from databases in companies such as 23andMe, AncestryDNA, Living DNA, HomeDNA, National Geographic Genographic Project, or MyHeritageDNA. With genetic tests, a patient's cheek can be swabbed or scraped, or spit can be collected to analyze the DNA in order to determine if cancer or viruses are present. Other genetic tests can be performed to collect additional information regarding viruses and cancer within the body that may not be obtainable from a swab or spit from samples such as, but not limited to, blood, plasma, urine, other fluids, or tissue samples from biopsies.

Various imaging can be collected, such as, but not limited to, CAT scans, CT scans, X-rays, MRI, ultrasounds, PET scans, or other visual analyses. Reports from imaging studies are analyzed and encoded using an NLP algorithm to extract features. These features, along with structured findings from a radiologist are used to inform the model.

Unstructured data can also be collected, such as, but not limited to, any patient notes over time. Natural language can be processed into a network of classifiers to identify propensities for certain risk factors, given certain patient notes. For example, there may be a correlation between the presence of hygiene concerns in a patient note and reduced likelihood of adherence to a drug therapy regime. Unstructured patient data includes notes by healthcare professionals as well as information collected directly from the patient including responses questionnaires, intake forms, etc.

This patient data structure, when fully populated, contains the full digital footprint needed to make queries into the logic engine. Instead of a fixed patient data structure, the patient model is fluid, and its makeup of fields is determined by the desired outcome of the model. This reflects the fluidity of the patient's stasis as the patient's condition ultimately requiring the need for multiple drug consumption and the related dosing is fluid as the patient initially succumbs to a disease, is treated with the drugs, and then hopefully recovers from the disease. As the patient's stasis changes and hopefully returns to homeostasis, dosing can be altered.

The logic engine can request supplemental data 13 based on the patient data. Once trained, the logic engine has the ability to apply a discrete weighting regime to extracted features 28 based on their significance, i.e., request a blood level or demographic data point prior to making a dosing recommendation, imaging, pharmacogenomics testing, lifestyle questions, or any other type of diagnostics required. Different drug combinations will require different sets of supplemental data. Additional data selection can be weighted by importance, invasiveness, cost, and availability. For example, if a certain test is not available or prohibitively invasive, the logic engine reacts accordingly by being transparent with the decreased accuracy or exposure to potential risk.

Since the required input data varies on numerous conditions, essential data points are unknown until the basic query has started. If no further data is needed, the logic of the present invention can continue without additional input. Also, data can be weighted, and combinations of data can be weighted.

Figure 5:
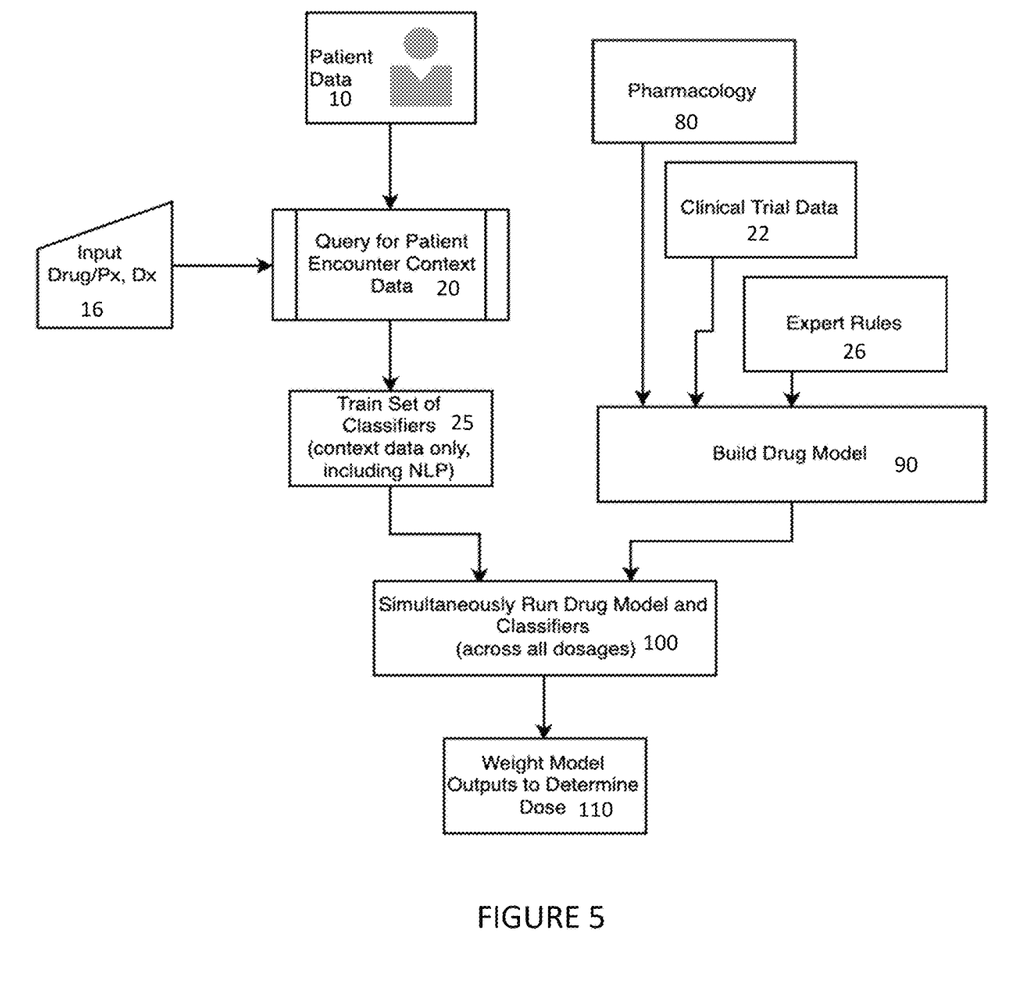
FIG. 5 is a schematic of the method of the present invention.

The database 50 can also collect information relating to the drugs desired to be prescribed (i.e., pharmacology information 80, shown in FIG. 5). Pharmacology information 80 can include drug mechanism of action, the safe dosage range, the suggested dosing strategy, and other pharmacological properties such as liberation, absorption, distribution, metabolism, and excretion. These factors and any other available information are taken into consideration to develop the drug-based model.

Prescriptions of certain drugs (or combinations of drugs) can require pharmacogenomic testing to check for certain markers. These markers can help decide between different classes of drug, circumvent known risk factors, as well as optimize the dosages. Since the effectiveness of a therapy is influence by the presence of certain markers, the results from genetic testing can be critical inputs. Pharmacogenomic testing is widely used when evaluating medications used in the treatment of ADD/ADHD and depression, anticoagulants, and others. The use and availability of data from pharmacogenomic testing is on the rise due to decreasing costs.

Mimicking the human expert decision making process, all data pertinent to making an informed decision must be made available and formatted prior to running the logic engine. The logic engine can proceed with missing data points, however, accuracy and therefore confidence in the decision are reduced.

Nearest neighbor data can be identified 21. A key aspect to the success of the present invention is the use of data from similar patient data markers. A "nearest neighbor", as used herein, can be persons that have similar patient data and/or underwent a treatment plan with similar drug combinations. Identifying existing records similar to the patient in treatment is a key component to the accuracy of the logic engine. A multi-dimensional nearest neighbor algorithm is used to find those individuals from existing sets, i.e., a K-Nearest Neighbor (KNN) algorithm. The KNN algorithm is a clustering algorithm and acts as a non-parametric untrained classifier that evaluates the overall similarity between two patients/subjects based on the degree of differences across multiple features. The flexibility of such an algorithm allows consideration of many parameters when searching for pertinent context data. Weights on certain factors can vary depending on the type of diagnosis and class of drug. For example, a patient might be more willing to risk side effects in exchange for efficacy. These similar patient profiles are grouped into subsets to look for trends that can be used to optimize the treatment plan of the given patient. While the KNN algorithm can be preferred, other clustering algorithms can also be used, such as, but not limited to, K-Means, Affinity Propagation, Mean Shift, Spectral Clustering, Support Vector Machines. One advantage of KNN over other techniques is that it is easily scalable across many dimensions. Further, from case-to-case the differing dimensions and weights are easily included. Nearest neighbors can also be identified from genetic testing databases who have also been treated for similar diseases or with similar treatments.

The purpose of the KNN algorithm is to find patients most similar to the present patient. Once identified, the "neighboring" patient data, including treatment plan and outcome, are used to evaluate the present subject. To make the identification, the differences are evaluated in each parameter comprising the patient data structure. While most commonly used with continuous values (weight, age, LDL level, etc.), the algorithm can be used with discrete values as well (race/ethnicity, familial history, presence of certain symptoms, etc.). The differences across each parameter are combined using a weighting scheme such that a normalized 'distance' is produced representing an overall difference metric between two patients. The distance calculation between two patients is achieved using a regression-type KNN algorithm. Key to the regression evaluations is the Mahalanobis distance. The Mahalanobis distance evaluates to a Euclidian distance since the covariance matrix is always the identity matrix, i.e., one parameter in this case is never to be compared independently with another parameter. The benefit of adapting the Mahalanobis distance instead of using pure Euclidian distance is that Mahalanobis distance includes the measurement of the number of deviations away from the norm. While the actual standard deviation is not always ideal, an equivalent term is used.

If the present patient $P_1$ has a set of parameters where $P_1 = \{\mu_{1P1}, \mu_{2P1}, \mu_{3P1}, \ldots \mu_{NP1}\}$ and an arbitrary patient, $P_\beta$, where $P_\beta = \{\mu_{1P\beta}, \mu_{2P\beta}, \mu_{3P\beta}, \ldots \mu_{NP\beta}\}$, then the distance, D, between the two patients is:

$$D_1(P_1, P_\beta) = \sqrt{\sum_{i=1}^{N} (\mu_{iP1} - \mu_{iP\beta})^2}$$

Several adaptations are needed to the above generalized equation. Mainly, handling a weighting schema. Most simply, a set of weights, W, should be created with each parameter in P being assigned a weight. Weights can be applied using any technique. Shown below is an intuitive 1-10 linear weighting schema. If W={$\rho_1$, $\rho_2$, $\rho_3$, ... $\rho_N$}, then the distance, D, can be evaluated by:

$$D_2(P_1, P_\beta) = \sqrt{\sum_{i=1}^{N} \rho_i (\mu_{iP1} - \mu_{iP\beta})^2}$$

In the above examples for $D_1$ and $D_2$ continuous values are used for $\mu_N$. In this application, continuous values can be integers or rational numbers. Discrete values must be handled in a special manner. Since there is no intuitive value for the difference between two ethnicities, one must be manually supplied in a lookup table. Algorithmically, parameters with continuous values should be summated using the squared difference while parameters with continuous values are summated manually. The same W={$\rho_1$, $\rho_2$, $\rho_3$, ... $\rho_N$} weighting schema applies to discrete parameters as well.

The threshold for evaluating whether or not another patient is sufficiently similar to the present patient is situational. The ideal number of similar subjects is to be optimized on a case-to-case basis when there exists sufficient training data.

KNN algorithms have been used before. For example, U.S. Pat. No. 10,123,748 (IBM) discloses a Patient Risk Analysis method that uses KNN to find similar patients. U.S. Pat. No. 7,730,063 discloses a personalized medicine method that also mentions KNN as a potential algorithm for finding similar patients. The present invention's ability to include continuous and discrete parameters as well as customized weights in the KNN differentiates over these prior art methods.

The inputs to the logic engine are broad and complex. AI techniques such as the KNN algorithm are applied to the inputs to precondition the data. By taking this step to precondition data, the following processing steps are simplified.

The logic engine employs a combination of artificial intelligence techniques, both supervised and unsupervised. Instead of using a broad-scale program that is trained once, the logic engine in the present invention is unique to the inputs and is therefore trained on demand. The benefit to this technique is to emphasize the individuality of the patient and the symptoms.

Figure 3:
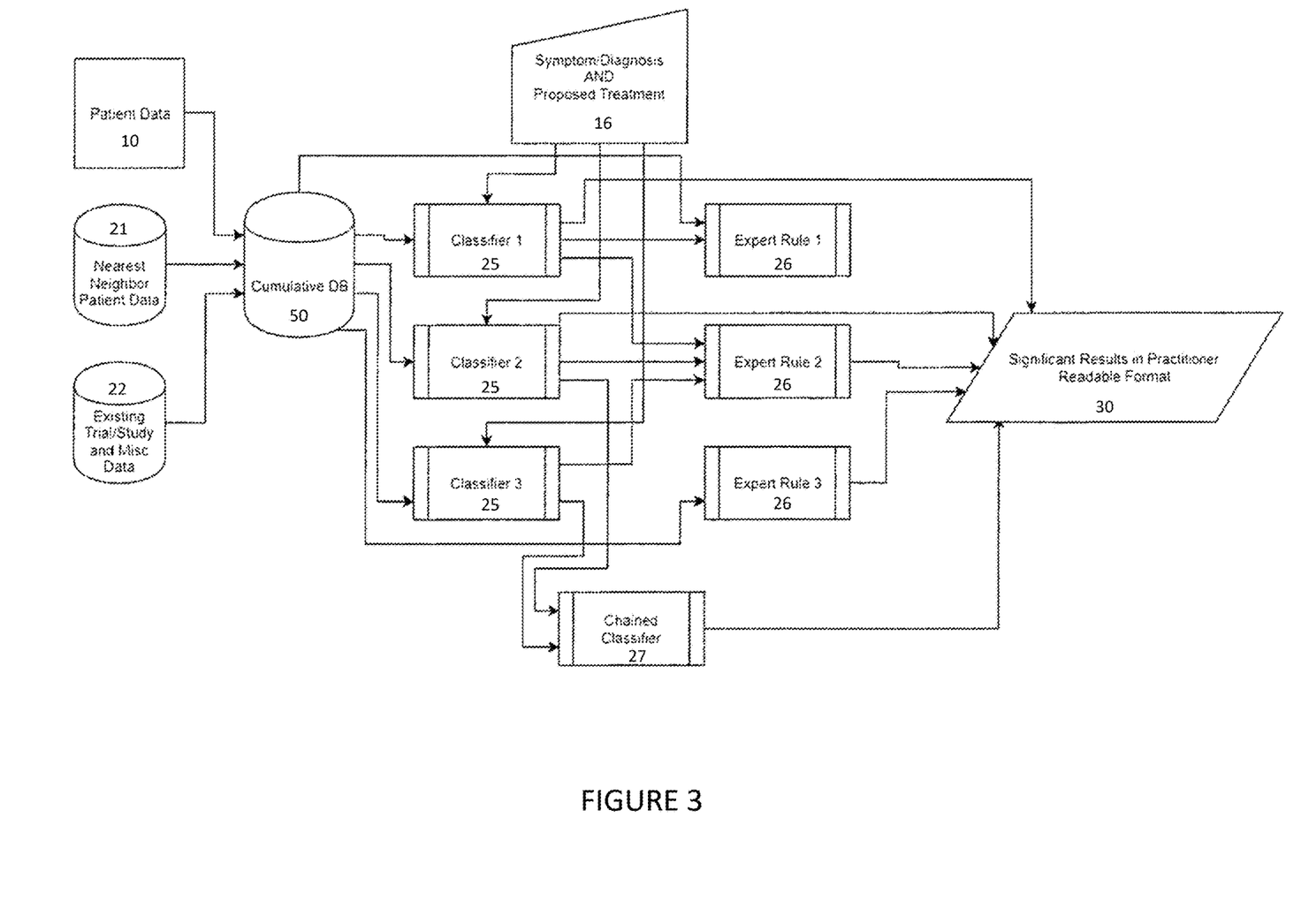
FIG. 3 is a schematic of classifiers and expert rules in the method.

Most broadly, and as shown in FIG. 3, the present invention includes model logic 29 composed of a series of classifiers 25, some of which offer direct outputs (such as the likelihood for an occurrence of a direct drug interaction or the presence of a certain side effect), while others perform intermediary steps. Classifiers 25 and expert rules 26 implemented in series is a strategy known as chaining 27, a process that takes advantage of the smaller preprocessing steps conducted by earlier-staged processing. Processing data using classifiers 25 in this way codes the patient information into a format suitable for use in existing artificial intelligence techniques. Most commonly, this involves assigning a quantitative element to inherently non-quantitative data. Data points, such as the presence of a side effect, are turned into features. Data elements can be Boolean or continuous depending on the type. Each individual data element is assigned a confidence and a weight. The confidence is a representation of the accuracy of the element, while the weight represents the importance.

The expert system also contains a series of rules 26 prepopulated by practitioners. These rules 26 can be drug or drug-class specific and compose the supervised learning aspect of the AI. In the spirit of fuzzy logic systems, each rule 26 is assigned a varying degree of truth, establishing a crude weighting scheme.

The classifiers 25 and the drug model 90 are ran simultaneously across all possible dosage ranges 100. For each dosage, classifications with confidence intervals are calculated. The generic drug model is ran using the same set of dosages mapped out to the same classifiers used when evaluating context data. The outputs from both models are weighted and combined to determine the optimal dose 110 in the output 30.

A major differentiator with the present invention relates to the mimicked expert output 30 of the logic engine. The output of the logic engine is an overall comprehensive analysis of the present patient, the diagnosis, and the primary method of treatment with dosages for each diagnosis. Any notable findings related to drug interaction, decreased efficacy, or side effect management are incorporated into the output. In this way, the full treatment plan is considered rather than the industry status quo of evaluating the possibility of toxicity or otherwise adverse reaction. It accomplishes producing an output based on data not accessible by the practitioner or pharmacist. Analysis is provided to determine output presently not considered by the practitioner. Presently, the only assistance to the practitioner or pharmacist is in the nature of do or do not do. That is, do give certain drugs together or do not based on general know toxicities. Nothing is available that assists in not only minimizing toxicity, but also maximizing efficacy of drug combinations.

The format of the output 30 can be a practitioner readable report with information being displayed in a manner to easily allow the user to identify categories of alerts. Certain outputs 30 can alter the course of a treatment altogether while other times an output might reinforce a direction in an attempt to mitigate an already known side effect. When applicable, the likelihood or confidence approximation is presented as well. This transparent output 30 format is all in an attempt to synthesize relative information when the practitioner is facing a treatment decision.

The output 30 can also be sent to a pharmacy or self-dispensing machine where the determined dose of each drug can be prepared for the patient 40. The output 30 can also provide the patient with instructions of how to take each drug and side effects to watch out for, as well as contraindications with commonly taken over the counter medications, supplements, and food. The output 30 can be sent wirelessly to any medical professional or the patient to read on a mobile device, tablet, laptop, or desktop computer. While doctors can use the logic engine to initially prescribe drugs at a certain dose to a patient, the logic engine can also be used by pharmacists to check a doctor's prescription in view of the other drugs that the patient is currently taking to make sure that the dose is correct and to reduce side effects.

The database 50 can further be in electronic communication with an insurance company's databases 60 and have access to a particular patient's insurance plan. Once a particular dose of the drug combination has been determined, the logic engine can further analyze the feasibility of the patient taking the particular combination of drugs according to what their insurance will cover. The logic engine can determine costs for the patient and determine if a generic drug is available for a particular input drug, or if a similar working drug that costs less is available. If a similar lower-cost drug is available, the logic engine can provide optimal dosing for that drug as a substitute as well as any information regarding side effects or efficacy as compared to the original input drug.

The database 50 can also be in electronic communication with drug administration devices 70. This can be to the extent of real time dosing, administration, patient data gathering, and dosing adjustment based on the real time data. In other words, after running the logic engine, and based on the recommended doses of drugs taken by the patient, the drug administration device 70 can receive updated dose information and adjust future doses accordingly. Electronic communication can be wireless or wired (such as with BLUETOOTH® or downloadable with a USB connection) and signals can be sent at the time that a dose is administered. These devices can include, but are not limited to, transdermal patches, intravenous drips, self-injection and auto-injection devices, wearable injection devices, and implantable drug delivery devices.

In one specific embodiment, any of the genetic information gathered from the patient as described above can be used to design a gene editing treatment specific for the patient as a suggested output 30. In particular, gRNAs (preferably two or more) corresponding to a target DNA or RNA of a virus or cancer (or any unwanted genetic sequence within the body) can be designed specifically for the patient to be used along with a gene editor (RNA-guided endonuclease) treatment. The gene editor can be zinc finger nuclease, TALENs (transcription activator-like effector nucleases), argonaute protein, human WRN, C2c2, C2c1, C2c3, CRISPR Cas9, CRISPR/Cpf1, CRISPR/TevCas9, Archaea Cas9 (ARMAN 1, ARMAN 4), CasX, or CasY. The gene editor can be delivered by vector or nanovesicle, and preferably excises (i.e., removes completely) the undesired DNA or RNA from the body such as described in U.S. Pat. No. 9,981,020 to Khalili, et al. This method provides a personalized treatment for the patient using the algorithm of the present invention to determine both the correct dosing information and the correct target information based on the genetic testing information input in the algorithm. Using the algorithm can result in fewer off target effects in the patient because a lower dose can be given to achieve the desired results.

Therefore, the present invention provides for a method of treating a patient, by collecting patient data including genetic testing information, analyzing the data in view of dosing criteria established based on outside data, designing gRNAs for use with a gene editor treatment based on the genetic testing information, and determining a dose for the gene editor treatment.

The virus targeted can be a lysogenic virus such as hepatitis A, hepatitis B, hepatitis D, HSV-1, HSV-2, cytomegalovirus, Epstein-Barr virus, Varicella Zoster virus, HIV1, HIV2, HTLV1, HTLV2, Rous Sarcoma virus, HPV virus, yellow fever, zika, dengue, West Nile, Japanese encephalitis, lyssa virus, vesiculovirus, cytohabdovirus, Hantaan virus, Rift Valley virus, Bunyamwera virus, Lassa virus, Junin virus, Machupo virus, Sabia virus, Tacaribe virus, Flexal virus, Whitewater Arroyo virus, ebola, Marburg virus, JC virus, and BK virus. The virus targeted can be a lytic virus such as hepatitis A, hepatitis C, hepatitis D, coxsachievirus, HSV-1, HSV-2, cytomegalovirus, Epstein-Barr virus, varicella zoster virus, HIV1, HIV2, HTLV1, HTLV2, Rous Sarcoma virus, rota, seadornvirus, coltivirus, JC virus, and BK virus. The virus can also be a combination of lysogenic and lytic.

The cancer targeted can be, but is not limited to, cancer cells associated with adenoid cystic carcinoma, adrenal gland tumors, amyloidosis, anal cancer, appendix cancer, astrocytoma, ataxia-telangiectasia, attenuated familial adenomatous polyposis, Beckwith-Wiedermann Syndrome, bile duct cancer, Birt-Hogg-Dube Syndrome, bladder cancer, bone cancer, brain stem glioma, brain tumors, breast cancer, carcinoid tumors, Carney complex, central nervous system tumors, cervical cancer, colorectal cancer, Cowden syndrome, craniopharyngioma, desmoplastic infantile ganglioglioma, endocrine tumors, ependymoma, esophageal cancer, Ewing sarcoma, eye cancer, eyelid cancer, fallopian tube cancer, familial adenomatous polyposis, familial malignant melanoma, familial non-VHL clear cell renal cell carcinoma, gallbladder cancer, Gardner Syndrome, gastrointestinal stromal tumor, germ cell tumor, gestational trophoblastic disease, head and neck cancer, diffuse gastric cancer, leiomyomatosis and renal cell cancer, mixed polyposis syndrome, pancreatitis, papillary renal cell carcinoma, HIV and AIDS-related cancer, islet cell tumors, juvenile polyposis syndrome, kidney cancer, lacrimal gland tumor, laryngeal and hypopharyngeal cancer, acute lymphoblastic leukemia, acute lymphocytic leukemia, acute myeloid leukemia, B-cell prolymphocytic leukemia, hairy cell leukemia, chronic lymphocytic leukemia, chronic myeloid leukemia, chronic T-cell lymphocytic leukemia, eosinophilic leukemia, Li-Fraumeni Syndrome, liver cancer, lung cancer, Hodgkin lymphoma, Non-Hodgkin lymphoma, Lynch Syndrome, mastocytosis, medulloblastoma, melanoma, meningioma, mesothelioma, Muir-Torre Syndrome, multiple endocrine neoplasia type 1, multiple endocrine neoplasia type 2, multiple myeloma, myelodysplastic syndromes, MYH-associated polyposis, nasal cavity and paranasal sinus cancer, nasopharyngeal cancer, neuroblastoma, neuroendocrine tumors, neurofibromatosis type 1, neurofibromatosis type 2, nevoid basal cell carcinoma syndrome, oral and oropharyngeal cancer, osteosarcoma, ovarian cancer, pancreatic cancer, parathyroid cancer, penile cancer, Peutz-Jeghers Syndrome, pituitary gland tumors, pleuropulmonary blastoma, prostate cancer, retinoblastoma, rhabdomyosarcoma, salivary gland cancer, sarcoma, alveolar soft part and cardiac sarcoma, Kaposi sarcoma, skin cancer, small bowel cancer, stomach cancer, testicular cancer, thymoma, thyroid cancer, tuberous sclerosis syndrome, Turcot Syndrome, unknown primary, uterine cancer, vaginal cancer, Von Hippel-Lindau Syndrome, Wilms tumors, or Xeroderma pigmentosum.

The present invention has several advantages over the prior art. Many current pharmacology related software checks for known high-level interactions between two specific drugs or drug classes. Going beyond that simple check, the present invention checks nearest neighbor patient outcomes when given similar drug combinations. Even if there is no indicated complication, a decrease in efficacy or increase in side effects are considered.

Further, outputs of the exam are never limited to an amount of active ingredient, instead, full treatment plans are suggested. This information can be relayed to the patient or used internally for the decision-making process. Therefore, the present invention provides a technical effect of providing a treatment plan with dosing of particular drugs to the patient, as well as providing to the patient the recommended doses. There is potential to maximize a treatment plan while acting in accordance with the suggested use of the drug. Varying treatment plans can be justified if trends suggest preferred outcomes for similar patient profiles. Instead of the present invention being treated as a dosage calculator, it is more so a decision-making tool that puts forth all necessary information to the practitioner to make a more informed treatment plan.

The present invention provides advantages to patients because instead of being prescribed drug combinations at sub optimal and sometimes sub efficacious levels to avoid toxicity and then being dosed up to efficacy while hopefully avoiding toxicity, the present invention can initially dose single or multiple drugs to a patient at nontoxic and efficacious doses. Thereby, the patient is immediately treated (critical in acute situations such as stroke, seizures, arrhythmia, etc.), while avoiding toxicity.

The present invention provides advantages to physicians because they no longer have to guess at dosing, especially in situations of prescribing multiple interacting drugs. The platform also considers the patient's clinical and physical conditions thereby personalizing the patient's prescription.

The present invention provides advantages to pharmaceutical companies due to avoidance of adverse effects related to either drugs toxicity or apparent inefficacious use of recommended therapeutics. There are also drug development benefits. The platform can be used to analyze early clinical study data to define a preferred study class for a Phase 3 study. The risk of study failure is greatly reduced.

The present invention provides advantages to insurers by decreasing potential malpractice cases against physicians based on alleged improper prescription practices. Pharmaceutical companies will benefit for the same reasons. More important is that drugs, especially in multi-prescription situations, can be prescribed to more efficiently be efficacious. Many drugs are under-dosed by physicians afraid of toxicity issues, especially in chronic dosing situations. This results in false negative results and patient failure. Insurance providers are unjustly penalized under those situations. The added cost of the implementation of the platform will be greatly outweighed by the financial benefit and practical benefit to the patient. This removes sometimes unjust prejudice to the pharma brand, adding value to the pharma industry.

The present invention can be useful in dosing any combination of drugs. The drugs can be generally from the classes antihistamines, anti-infective agents, antineoplastic agents, autonomic drugs, blood derivatives, blood formation agents, coagulation agents, thrombosis agents, cardiovascular drugs, cellular therapy, central nervous system agents, contraceptives, dental agents, diagnostic agents, disinfectants, electrolytic, caloric, and water balance, enzymes, respiratory tract agents, eye, ear, nose, and throat preparations, gold compounds, heavy metal antagonists, hormones and synthetic substitutes, oxytocics, radioactive agents, serums, toxoids, and vaccines, skin and mucous membrane agents, smooth muscle relaxants, and vitamins. Some specific combinations of drugs that are most commonly used by people include, but are not limited to, lisinopril and atorvastatin, lisinopril and metformin, amlodipine and lisinopril, alprazolam and amphetamine salt combo, amphetamine salt combo and amphetamine salt combo xr, hydrocodone/acetaminophen and alprazolam, amlodipine and atorvastatin, lisinopril and hydrochlorothiazide, atorvastatin and clopidogrel, atorvastatin and metformin, metformin/lisinopril/atorvastatin, clopidogrel/atorvastatin/lisinopril, glipizide/metformin/lisinopril, atorvastatin/amlodipine/lisinopril, amlodipine/hydrochlorothiazide/lisinopril, carvedilol/atorvastatin/lisinopril, atorvastatin/metoprolol/lisinopril, clopidogrel/metoprolol/atorvastatin, lisinopril/carvedilol/furosemide, and amlodipine/metformin/lisinopril.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology, which has been used is intended to be in the nature of words of description rather than of limitation.

Obviously, many modifications and variations of the present invention are possible in light of the above teachings. It is, therefore, to be understood that within the scope of the appended claims, the invention can be practiced otherwise than as specifically described.

What is claimed is:

1. A method for dosing multiple drugs for an individual patient and treating the patient with a gene editor treatment, including the steps of:

a healthcare professional collecting and inputting data from the individual patient including drugs to be taken by the patient and genetic testing information into a database with a central artificial intelligence (AI) stored on non-transitory computer readable media, wherein the AI has access to otherwise private outside data, the collecting step including the healthcare professional collecting a sample from the individual patient chosen from the group consisting of spit, blood, plasma, urine, and tissue and obtaining genetic data and determining that the individual patient has cancer or a virus;

after receiving the individual patient data, the central AI analyzing the individual patient data in view of dosing criteria established based on the outside data including clinical trial data from outside databases of clinics, electronic medical records, pharmaceutical companies, private databases, and contract research organizations (CROs);

the central AI performing the analyzing step by the AI extracting all features relating variables that affect drug metabolism and creating a model relating dosing to patient condition and effect of drugs on the condition that affect efficacy and toxicity of all drugs taken, wherein the variables include age of patient, weight of patient, known side effects of drugs alone and in combinations with other drugs, known toxicity range as related to ED 50 and dose response points of interest, efficacy ranges, and chronic treatment effect versus acute treatment, the AI conducting natural language processing on unstructured data and extracting features from unstructured text of patient notes and notes from informal exams, after extracting all features and creating a model, the AI identifying nearest neighbors of persons from the outside data having similar patient data and genetic data and/or underwent a treatment plan with similar drug combinations and identifies related study and trial data with a K- Nearest Neighbor algorithm that calculates a distance between the patient and a neighbor patient using both continuous data and discrete data that is assigned a value and manually supplied to the database, after identifying nearest neighbors, the AI comparing patient data to neighboring patient data with weighting schemes, and wherein genetic testing information generates ethnicity and demographics features for the K-Nearest Neighbor algorithm, and the AI running the model simultaneously across all possible dosage ranges;

after the central AI performing the analyzing step, the central AI determining doses of multiple drugs for each drug taken by the individual patient and maximizing therapeutic effect while minimizing adverse effects for the interaction of specific drugs or drug classes taken while minimizing cost to the patient, taking into account insurance coverage, patient preferences, and availability of the drugs, and displaying the dose in a readable report for a practitioner; and based on the readable report, a healthcare professional providing a personalized gene editor editing treatment to the individual patient with dosing and targeting information based on the genetic testing information input into the central AI; and designing gRNAs for use with the gene editor treatment for a virus or cancer based on the genetic testing information, wherein the gene editor is chosen from the group consisting of zinc finger nuclease, TALENs (transcription activator-like effector nucleases), argonaute protein, human WRN, C2c2, C2c1, C2c3, CRISPR Cas9, CRISPR/Cpf1, CRISPR/TevCas9, Archaea Cas9 (ARMAN 1, ARMAN 4), CasX, and CasY, and treating the individual patient with the gene editor treatment.

2. The method of claim 1, further including the step of dispensing the multiple drugs to the individual patient.

3. The method of claim 1, wherein the individual patient data and outside data is chosen from the group consisting of pharmacokinetics, distribution, prior toxicity and efficacy determinations, age, metabolism, and combinations thereof.

4. The method of claim 1, wherein said collecting step is further defined as collecting symptoms, diagnoses, proposed drugs and treatments, fixed demographics, temporal values, imaging, imaging reports, and unstructured data and wherein genetic testing information is collected from databases of 23andMe, AncestryDNA, Living DNA, HomeDNA, National Geographic Genographic Project, and MyHeritageDNA, and from biological samples of the patient.

5. The method of claim 1, wherein the virus is chosen from the group consisting of hepatitis A, hepatitis B, hepatitis C, hepatitis D, coxsachievirus, HSV-1, HSV-2, cytomegalovirus, Epstein-Barr virus, Varicella Zoster virus, HIV1, HIV2, HTLV1, HTLV2, Rous Sarcoma virus, rota, seadornvirus, coltivirus, HPV virus, yellow fever, zika, dengue, West Nile, Japanese encephalitis, lyssa virus, vesiculovirus, cytohabdovirus, Hantaan virus, Rift Valley virus, Bunyamwera virus, Lassa virus, Junin virus, Machupo virus, Sabia virus, Tacaribe virus, Flexal virus, Whitewater Arroyo virus, ebola, Marburg virus, JC virus, and BK virus.

6. The method of claim 1, wherein the cancer is chosen from the group consisting of adenoid cystic carcinoma, adrenal gland tumors, amyloidosis, anal cancer, appendix cancer, astrocytoma, ataxia-telangiectasia, attenuated familial adenomatous polyposis, Beckwith-Wiedermann Syndrome, bile duct cancer, Birt-Hogg-Dube Syndrome, bladder cancer, bone cancer, brain stem glioma, brain tumors, breast cancer, carcinoid tumors, Carney complex, central nervous system tumors, cervical cancer, colorectal cancer, Cowden syndrome, craniopharyngioma, desmoplastic infantile ganglioglioma, endocrine tumors, ependymoma, esophageal cancer, Ewing sarcoma, eye cancer, eyelid cancer, fallopian tube cancer, familial adenomatous polyposis, familial malignant melanoma, familial non-VHL clear cell renal cell carcinoma, gallbladder cancer, Gardner Syndrome, gastrointestinal stromal tumor, germ cell tumor, gestational trophoblastic disease, head and neck cancer, diffuse gastric cancer, leiomyomatosis and renal cell cancer, mixed polyposis syndrome, pancreatitis, papillary renal cell carcinoma, HIV and AIDS-related cancer, islet cell tumors, juvenile polyposis syndrome, kidney cancer, lacrimal gland tumor, laryngeal and hypopharyngeal cancer, acute lymphoblastic leukemia, acute lymphocytic leukemia, acute myeloid leukemia, B-cell prolymphocytic leukemia, hairy cell leukemia, chronic lymphocytic leukemia, chronic myeloid leukemia, chronic T-cell lymphocytic leukemia, eosinophilic leukemia, Li-Fraumeni Syndrome, liver cancer, lung cancer, Hodgkin lymphoma, Non-Hodgkin lymphoma, Lynch Syndrome, mastocytosis, medulloblastoma, melanoma, meningioma, mesothelioma, Muir-Torre Syndrome, multiple endocrine neoplasia type 1, multiple endocrine neoplasia type 2, multiple myeloma, myelodysplastic syndromes, MYH-associated polyposis, nasal cavity and paranasal sinus cancer, nasopharyngeal cancer, neuroblastoma, neuroendocrine tumors, neurofibromatosis type 1, neurofibromatosis type 2, nevoid basal cell carcinoma syndrome, oral and oropharyngeal cancer, osteosarcoma, ovarian cancer, pancreatic cancer, parathyroid cancer, penile cancer, Peutz-Jeghers Syndrome, pituitary gland tumors, pleuropulmonary blastoma, prostate cancer, retinoblastoma, rhabdomyosarcoma, salivary gland cancer, sarcoma, alveolar soft part and cardiac sarcoma, Kaposi sarcoma, skin cancer, small bowel cancer, stomach cancer, testicular cancer, thymoma, thyroid cancer, tuberous sclerosis syndrome, Turcot Syndrome, unknown primary, uterine cancer, vaginal cancer, Von Hippel-Lindau Syndrome, Wilms tumors, and Xeroderma pigmentosum.

7. A logic engine for dosing multiple drugs and providing a gene editor treatment, comprising an algorithm stored on non-transitory computer readable media for collecting clinical trial data from outside databases of clinics, electronic medical records, pharmaceutical companies, private databases, and contract research organizations (CROs) to establish criteria for dosing multiple drugs to an individual patient and storing the outside data and individual patient data including genetic testing information in a database, the individual patient data including genetic data obtained from a sample from the individual patient chosen from the group consisting of spit, blood, plasma, urine, and tissue indicating that the individual patient has cancer or a virus, wherein after receiving the individual patient data, the algorithm analyzing the individual patient data in view of criteria established from the clinical trial data with artificial intelligence (AI), wherein the AI, having access to otherwise private outside data, then extracts all features relating variables that effect drug metabolism and creates a model relating dosing to patient condition and effect of drugs on the condition that effect efficacy and toxicity of all drugs taken, wherein the variables include age of patient, weight of patient, known side effects of drugs alone and in combinations with other drugs, known toxicity range as related to ED 50 and dose response points of interest, efficacy ranges, and chronic treatment effect versus acute treatment, and the AI conducts natural language processing on unstructured data and extracts features from unstructured text of patient notes and notes from informal exams, wherein after extracting all features and creating a model the AI identifies nearest neighbors of persons from the outside data having similar patient data and genetic data and/or underwent a treatment plan with similar drug combinations and identifies related study and trial data with a K-Nearest Neighbor algorithm that calculates a distance between the patient and a neighbor patient using both continuous data and discrete data that is assigned a value and manually supplied to the database, wherein after identifying nearest neighbors the AI compares patient data to neighboring patient data with weighting schemes, and wherein genetic testing information generates ethnicity and demographics features for the K-Nearest Neighbor algorithm, and the AI running the model simultaneously across all possible dosage ranges, and after running the model the algorithm determining a dose for each drug to be taken while considering interaction of specific drugs or drug classes taken while minimizing cost to the patient, considering insurance coverage, patient preferences, and availability of the drugs, wherein said algorithm provides an output in the form of a practitioner readable report, with the readable report providing a personalized gene editor editing treatment for the individual patient with dosing and targeting information based on the genetic testing information input into the AI that allows for designing gRNAs for use with the gene editor treatment for a virus or cancer based on the genetic testing information, wherein the gene editor is chosen from the group consisting of zinc finger nuclease, TALENs (transcription activator-like effector nucleases), argonaute protein, human WRN, C2c2, C2c1, C2c3, CRISPR Cas9, CRISPR/Cpf1, CRISPR/TevCas9, Archaea Cas9 (ARMAN 1, ARMAN 4), CasX, and CasY, and treating the individual patient with the gene editor treatment.

8. The logic engine of claim 7, wherein information flows in said algorithm is defined as from data input to the AI to and from a healthcare professional.

9. The logic engine of claim 8, wherein said healthcare professional is chosen from the group consisting of MD, pharmacist, hospital, insurer, nurse, and laboratory professional, and wherein said healthcare professional inputs data including patient data from monitors, data from EMRs, and insurance information, and wherein the AI integrates patient data with external systems for real-time decision making.

10. The logic engine of claim 7, wherein said logic engine can request supplemental data based on the individual patient data and wherein said database collects information relating to the multiple drugs including drug mechanism of action, safe dosage range, suggested dosing strategy, liberation, absorption, distribution, metabolism, and excretion.

11. The logic engine of claim 7, wherein said logic engine includes model logic having a series of classifiers and expert rules implemented in series, and said classifiers and a drug model are ran simultaneously across all possible dosage ranges, and outputs are weighted and combined to determine an optimal dose.

12. The logic engine of claim 7, wherein said logic engine provides said practitioner readable report to a place chosen from the group consisting of a pharmacy, a self-dispensing machine, a medical professional, and the individual patient, and wherein the practitioner readable report includes detailed analysis of drug interactions, insurance coverage, and cost considerations.

13. The logic engine of claim 7, wherein said logic engine is in electronic communication with an insurance company's databases and analyzes feasibility of said patient taking the particular combination of drugs according to what their insurance will cover.

14. The logic engine of claim 7, wherein said logic engine is in electronic communication with drug administration devices chosen from the group consisting of transdermal patches, intravenous drips, self-injection and auto-injection devices, wearable injection devices, and implantable drug delivery devices and wherein the electronic communication includes real-time adjustments based on patient feedback and monitoring.

15. The logic engine of claim 7, wherein genetic testing information is collected from databases of 23andMe, AncestryDNA, Living DNA, HomeDNA, National Geographic Genographic Project, and MyHeritageDNA, and from biological samples of the patient.

* * * * *